(12) United States Patent
Panse et al.

(10) Patent No.: US 11,547,489 B2
(45) Date of Patent: Jan. 10, 2023

(54) SHAPE SENSING OF MULTIPLE OVER-THE-WIRE DEVICES

(71) Applicant: KONINKLIJKE PHILIPS N.V., Eindhoven (NL)

(72) Inventors: Ashish Panse, Burlington, MA (US); Torre Michelle Bydlon, Melrose, MA (US); Paul Thienphrapa, Cambridge, MA (US); Molly Lara Flexman, Melrose, MA (US); Alexandru Patriciu, Belmont, MA (US); Sean Joseph Kyne, Brookline, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 897 days.

(21) Appl. No.: 16/345,331

(22) PCT Filed: Nov. 24, 2017

(86) PCT No.: PCT/IB2017/057376
§ 371 (c)(1),
(2) Date: Apr. 26, 2019

(87) PCT Pub. No.: WO2018/096491
PCT Pub. Date: May 31, 2018

(65) Prior Publication Data
US 2021/0282865 A1    Sep. 16, 2021

Related U.S. Application Data

(60) Provisional application No. 62/426,626, filed on Nov. 28, 2016.

(51) Int. Cl.
*A61B 34/20* (2016.01)
*A61B 17/00* (2006.01)

(52) U.S. Cl.
CPC ....... *A61B 34/20* (2016.02); *A61B 2017/0011* (2013.01); *A61B 2017/00084* (2013.01);
(Continued)

(58) Field of Classification Search
CPC .......... A61B 34/20; A61B 2017/00084; A61B 2017/0011; A61B 2034/2061;
(Continued)

(56) References Cited

U.S. PATENT DOCUMENTS 6,006,126 A * 12/1999 Cosman ............... G06V 10/245
600/417
6,102,926 A 8/2000 Tartaglia et al.
(Continued)

FOREIGN PATENT DOCUMENTS

JP    2014124302 A    7/2014
WO    2011141830 A1    11/2011

*Primary Examiner* — Sanjay Cattungal

(57) ABSTRACT

A medical instrument includes a first device (108) including shape-sensed flexible instrument, a second device (102) disposed over the first device and a third device (109) disposed over the first device and a portion of the second device. The second and third devices include a geometric relationship such that a position of the second device and the third device is determined from shape sensing information of the first device and the geometric relationship.

26 Claims, 5 Drawing Sheets

(52) U.S. Cl.
CPC ............... *A61B 2034/2061* (2016.02); *A61B 2562/0266* (2013.01)

(58) Field of Classification Search
CPC ............ A61B 2562/0266; A61B 90/96; A61B 2090/061; A61B 2090/3966; A61B 2505/05; A61B 2562/0204; A61B 5/065; A61B 5/1076; A61B 5/6852; A61B 2034/2059
See application file for complete search history.

(56) References Cited

U.S. PATENT DOCUMENTS

| | | | |
|---|---|---|---|
| 6,106,301 A | 8/2000 | Merril | |
| 6,471,710 B1 | 10/2002 | Bucholtz | |
| 9,962,066 B2 | 5/2018 | Rogers et al. | |
| 2003/0135102 A1 | 7/2003 | Burdette et al. | |
| 2005/0182319 A1 | 8/2005 | Glossop | |
| 2008/0147001 A1 | 6/2008 | Al-Marashi et al. | |
| 2010/0274085 A1 | 10/2010 | Mugan et al. | |
| 2012/0289843 A1 | 11/2012 | Chopra et al. | |
| 2013/0033700 A1* | 2/2013 | Hallil | A61N 5/1071 378/63 |
| 2013/0060146 A1* | 3/2013 | Yang | G01B 11/25 600/476 |
| 2013/0158512 A1 | 6/2013 | Gutierrez et al. | |
| 2013/0188855 A1 | 7/2013 | Desjardins et al. | |
| 2013/0204124 A1 | 8/2013 | Duindam et al. | |
| 2013/0310685 A1 | 11/2013 | Chan et al. | |
| 2014/0051987 A1 | 2/2014 | Kowshik et al. | |
| 2014/0187983 A1 | 7/2014 | Anderson | |
| 2016/0066794 A1* | 3/2016 | Klinder | A61B 5/02028 600/424 |
| 2016/0102969 A1* | 4/2016 | Verstege | A61B 1/009 250/206 |
| 2016/0228199 A1 | 8/2016 | Flexman et al. | |
| 2016/0331358 A1 | 11/2016 | Gordon | |
| 2018/0008351 A1* | 1/2018 | Schoenefeld | A61B 17/15 |
| 2018/0014886 A1 | 1/2018 | Flexman et al. | |
| 2018/0021097 A1* | 1/2018 | Quaid | A61B 34/35 600/407 |
| 2018/0279909 A1 | 10/2018 | Noonan et al. | |

\* cited by examiner

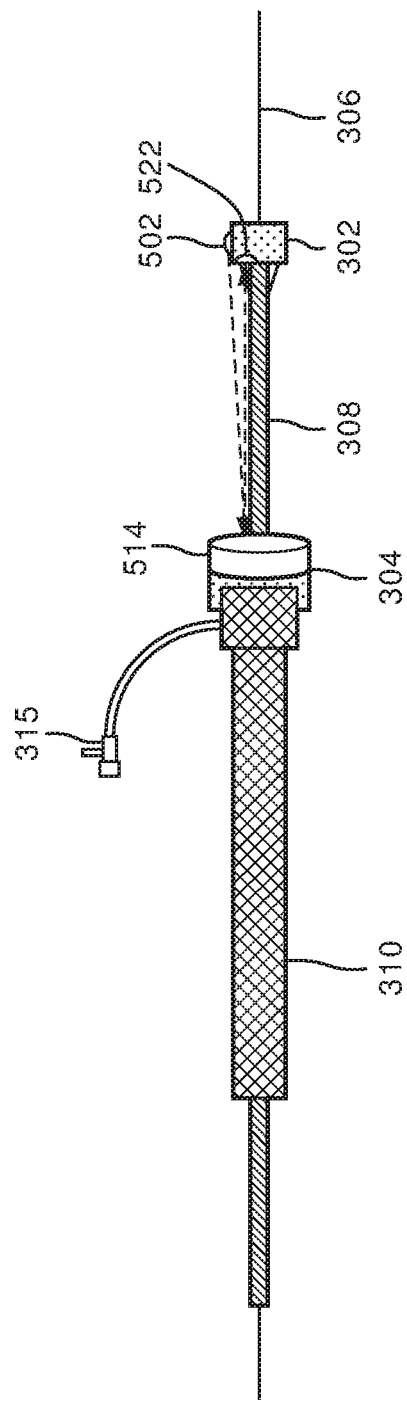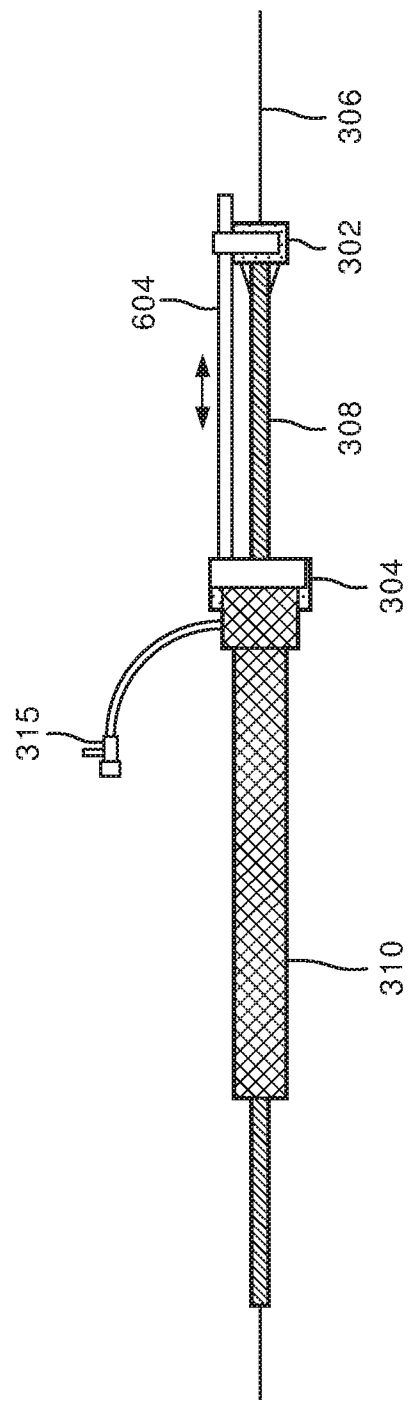

SHAPE SENSING OF MULTIPLE OVER-THE-WIRE DEVICES

CROSS-REFERENCE TO PRIOR APPLICATIONS

This application is the U.S. National Phase application under 35 U.S.C. § 371 of International Application Serial No. PCT/IB2017/057376, filed on Nov. 24, 2017, which claims the benefit of U.S. patent application Ser. No. 62/426,626, filed on Nov. 28, 2016. This application is hereby incorporated by reference herein.

BACKGROUND

Technical Field

This disclosure relates to medical instruments and more particularly to shape sensing in a wire device configured to sense multiple over-the-wire devices.

Description of the Related Art

A medical device such as a catheter, deployment system, or sheath is typically navigated inside the body with the use of fluoroscopy. Such devices are known as 'over-the-wire' devices as they are typically used in conjunction with a guidewire that travels through a lumen in the device. Optical shape sensing provides a 3D radiation-free navigation solution with the use of an optical fiber. These over-the-wire devices can be enabled with shape sensing by embedding an optical fiber(s) within the devices. This requires customizing a mechanical design of the device to add an additional lumen for the fiber. Adding the fiber and customizing the device would add cost and necessitate the use of an additional shape sensing system.

Optical shape sensing (OSS) or Fiber-Optical RealShape™ (also known as "Optical Shape Sensing", "Fiber Shape Sensing", "Fiber Optical 3D Shape Sensing", "Fiber Optic Shape Sensing and Localization" or the like) employs light along an optical fiber for device localization and navigation during surgical intervention. One principle involved makes use of distributed strain measurement in the optical fiber using characteristic Rayleigh backscatter or controlled grating patterns. Multiple optical fibers can be used together to reconstruct a 3D shape, or a single optical fiber with multiple cores that may also be helixed for a lower-profile sensor. The shape along the optical fiber begins at a specific point along the sensor, known as the launch or z=0, and the subsequent shape position and orientation are relative to that point. Optical shape sensing fibers can be integrated into medical devices to provide live guidance of the devices during minimally invasive procedures.

SUMMARY

In accordance with the present principles, a medical instrument includes a first device including a shape-sensed flexible instrument, a second device disposed over the first device and a third device disposed over the first device and a portion of the second device. The second and third devices include a geometric relationship such that positions of the second device and the third device are determined from shape sensing information of the first device and the geometric relationship.

A system with a plurality of over-the-wire devices includes a medical instrument including: a first device including a shape-sensed flexible wire; a second device disposed over the first device; and a third device disposed over the first device and a portion of the second device, the second and third device including a geometric relationship such that a position of the second device and the third device is determined from shape sensing information of the first device and the geometric relationship. A shape sensing module is coupled to the shape-sensed flexible wire to interpret the shape sensing information to determine positions of the second and third devices relative to the first device.

A method for determining positions of over-the-wire devices includes providing a medical instrument with a first device including a shape-sensed flexible instrument; a second device disposed over the first device; and a third device disposed over the first device and a portion of the second device; and determining a geometric relationship between the devices such that positions of the second device and the third device are determined from shape sensing information of the first device.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein:

FIG. 6 is a perspective view of a shape sensed device with a plurality of over-the-wire devices having a light measurement device mounted on the over-the-wire devices in accordance with one embodiment;

FIG. 7 is a perspective view of a shape sensed device with a plurality of over-the-wire devices having an encoded slider between the over-the-wire devices in accordance with one embodiment.

DETAILED DESCRIPTION OF EMBODIMENTS

Figure 1:
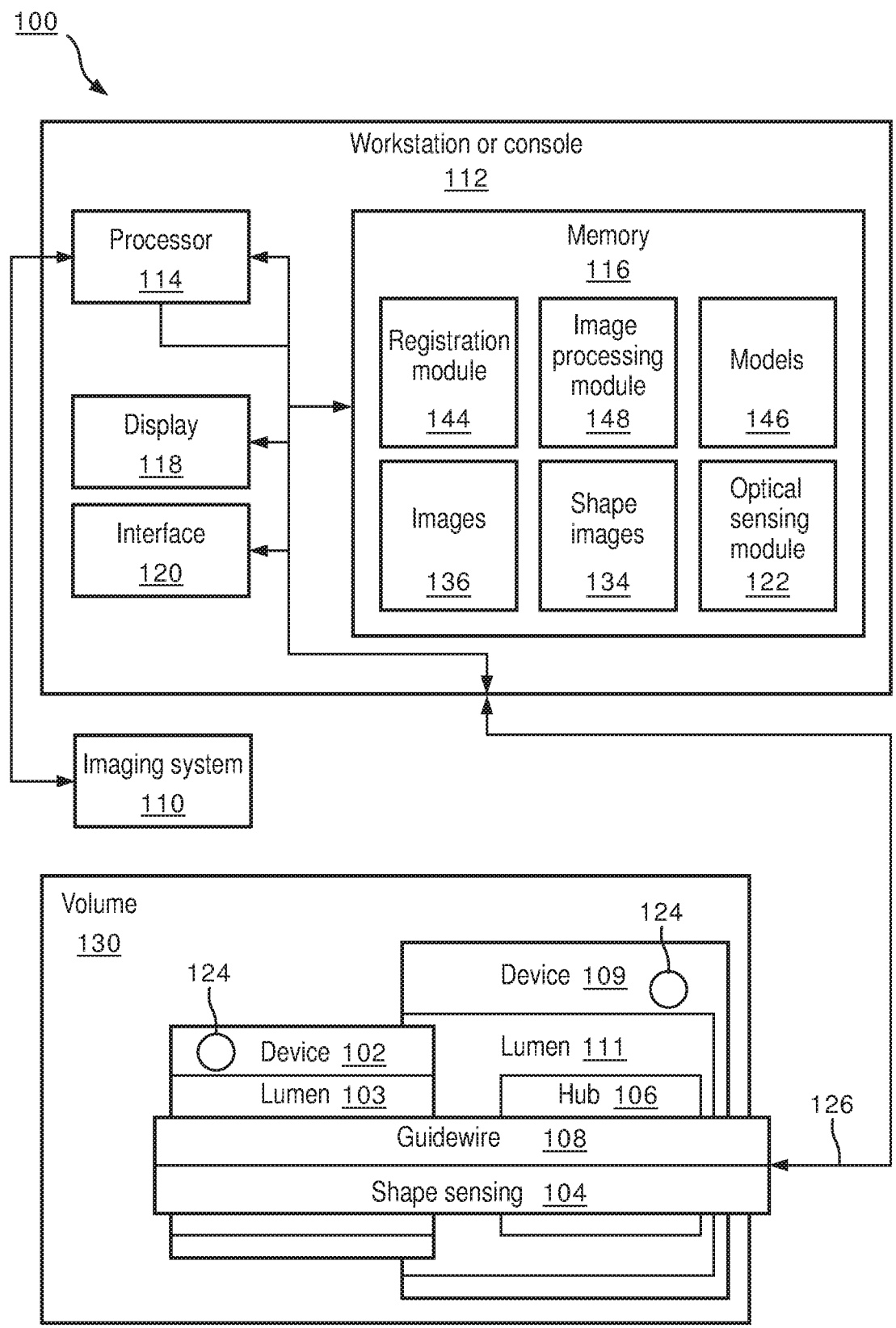
FIG. 1 is a block/flow diagram showing a shape sensing system measuring a shape sensed device and a plurality of over-the-wire devices without shape sensing in accordance with one embodiment.

In accordance with the present principles, a shape sensed guidewire or other flexible elongated device is provided for use in a lumen that also senses positions of multiple over-the-wire devices or components. If a catheter (or other deployable device) is employed over a shape sensed guidewire (or other flexible elongated device) then the guidewire shape also defines the catheter shape for the length over which the catheter overlaps the guidewire. The present embodiments permit virtual visualization of multiple over-the-wire devices that are run over a single shape sensed device (e.g., guidewire) without having to embed shape sensed fibers into all devices employed in a medical procedure.

A universal catheter hub is a fixture or device that can be applied to or employed with a medical instrument with shape sensing capabilities. The universal hub can be used to alter, deflect or orient the shape sensing device to provide a reference position in shape sensing data. A universal catheter hub may not be ideal for many types of devices. The universal catheter hub can rely on deforming the guidewire by applying a known curve onto a shape of the guidewire. It is more difficult to put a known curve into a catheter or sheath because the materials can be stiff and not easy to deform. Therefore, other methods can be employed to determine the location of another device on the guidewire (e.g., a third, fourth, etc. device).

For the purpose of ease of reference, the following convention will be employed throughout. Device 1 or the first device will refer to a shaped sensed flexible device (e.g., a shape sensed guidewire). Device 2 or the second device will refer to one of the devices placed over the first device (e.g., a navigation catheter). Device 3 or the third device will refer to the device placed over the second device and have the first device running therethrough (e.g., a sheath). In one example, the first device is a shape sensed wire, the second device is an over-the-wire device and the third device is an over-the-wire device placed over a portion of the second device. An operational relationship may exist between the second and the third devices such as a nested relationship, a slideable relationship, etc. This operational relationship can also be referred to generally as a geometric relationship.

If the shape sensed device (device 1) is employed, to properly define the position of a first non-shape-sensed device (e.g., catheter (device 2)) and a second non-shape-sensed device (e.g., device 3, e.g., a stent, graft, etc. over the catheter) along the guidewire, a relationship between the catheter, the other components and the guidewire needs to be known. The shape of a non-shape-sensed device (device 2) can be determined when the non-shape-sensed device runs over the shape-sensed guidewire (device 1) and locks onto an optional universal catheter hub with, e.g., a Luer lock or other mechanism. The shape of the non-shape-sensed device or devices will follow a same shape that is being measured by the shape-sensed device. A starting position is where the over-the-wire device (device 2 or device 3) locks onto the universal catheter hub. An ending position is based on a length of the device which can either be taken as the manufacturer's stated length or from a registration procedure. Multiple hubs can be connected to multiple over-the-wire devices (device 2 and device 3) and still run over the shape sensed device 1.

This can be achieved by using a hub device to cause the guidewire to take on a specific shape, curvature, or strain profile (shape profile) at a specific position along the catheter. A method to induce such a shape, curvature or strain profile is to employ the 'hub' with a known profile which can be stored as a template.

When a shape sensed device is inside a non-shape sensed device, the shape information from the sensed device can be used to infer information about the shape and position of the unsensed device. The registration needed may include a longitudinal translation between the two or more devices. This registration can be performed by using a known shape deformation of the sensed device at a specific location along the unsensed device or devices. The shape deformation can be detected through curvature detection, axial strain (from heating or tension), 2D or 3D shape matching, etc.

Multiple different versions of hub designs may be employed. In the case of hubs that use a shape deformation (as opposed to a strain deformation due to temperature, for example), the shape deformation will also define a plane. The same hub device can be used to track orientation of the device or devices (e.g., roll about its longitudinal axis). Orientation of the hub at a proximal part of the device(s) may map 1-to-1 to a therapeutic such as a balloon, valve, endograft, stent, etc. located in the distal portion.

The present principles describe hub designs that can be used to create a template profile. These designs may include, e.g., a Luer lock hub, an over-catheter hub, a hemostatic valve hub, among others. A hub may be defined as a component that can create a shape or curvature deformation in a shape sensed device, such as a guidewire. Such a component should be able to work in a wide range of commercially available medical devices within a clinical environment. The hub design can be employed across multiple device designs (e.g., a universal hub). Multiple different versions of hub designs can be used for deforming the guidewire and performing longitudinal encoding.

The over-the-wire devices can include a therapeutic such as a valve, endograft, stent, graft, etc. In endovascular aneurysm repair (EVAR), the position of the endograft needs to be known so that other catheters and endografts can be navigated with respect to an original endograft.

In accordance with one embodiment, devices and methods include registering a hub(s) or devices to a target node(s) of an over-the-wire device or devices and visualizing the over-the-wire devices in a display. A virtual model may be displayed on a display corresponding to a target node location in the over-the-wire device based on a position determined using the shape sensed guidewire. This permits any commercial catheter, deployment system, sheath, or other such device to be navigated using the shape sensed guidewire. In useful embodiments, devices and methods make use of a proximal hub to determine orientation of a distal portion of a device such as a commercially available catheter, deployment system, or sheath that is fitted over a shape sensing guidewire. The hub may include a shape profile that deflects the guidewire passing through it into a known shape. That shape can be detected along the fiber to know the longitudinal registration between the guidewire and the over-the-wire device. Since the hub is coupled to the over-the-wire device, the hub shape can also be used to track the rotation or position applied to the proximal part of the over-the-wire device. In addition, the relationship (e.g., geometric relationship) between over-the-wire devices can be employed to determine the positions and orientations of all the over-the-wire devices using the single shape sensed guidewire.

To provide a more efficient registration, the shape sensed device can utilize Fiber-Optical RealShape™ (FORS™ also known as "Optical Shape Sensing", "Fiber Shape Sensing", "Fiber Optical 3D Shape Sensing", "Fiber Optic Shape Sensing and Localization" or the like). A Fiber-Optical Real Shape™ system is a commercial name for systems developed by Koninklijke Philips, N.V. As used herein, the terms FORS™ and FORS™ systems are not, however, limited to products and systems of Koninklijke Philips, N.V., but refer generally to fiber optic shape sensing and fiber optic shape sensing systems, fiber optic 3D shape sensing, fiber optic 3D shape sensing systems, fiber optic shape sensing and localization and similar technologies.

It should be understood that the present invention will be described in terms of medical instruments; however, the teachings of the present invention are much broader and are applicable to any shape sensed instruments and instrument systems. In some embodiments, the present principles are employed in tracking or analyzing complex biological or mechanical systems. In particular, the present principles are applicable to internal tracking and navigation procedures of biological systems and procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for monitoring shape sensing enabled devices and other devices is illustratively shown in accordance with one embodiment. It should be understood that the present embodiments may include all or some of the elements depicted depending on the functionality of a given embodiment. System 100 may include a workstation or console 112 from which a procedure is supervised and/or managed. Workstation 112 preferably includes one or more processors 114 and memory 116 for storing programs and applications. Memory 116 may store an optical sensing module 122 configured to interpret optical feedback signals from a shape sensing device or system 104 (FORS™). Optical sensing module 122 is configured to use the optical signal feedback (and any other feedback) to reconstruct deformations, deflections and other changes associated with shape sensed devices.

In accordance with the present principles, an over-the-wire device or instrument (device 2) 102 includes a lumen 103, which receives a guidewire or other elongated flexible instrument 108 therein. A second over-the-wire device or instrument (device 3) 109 includes a lumen 111, which receives the guidewire or other elongated flexible instrument 108 therein, and can be configured to receive the over-the-wire device 102 or be configured to be disposed next to the over-the-wire device 102. The guidewire 108 is configured to receive the system 104 therethrough or thereabout. The devices 102 and 109 may include a catheter, a sheath, a probe, an endoscope, a robot, an electrode, a filter device, a balloon device, a graft, a stent, a drill, or other medical component having a lumen, etc. The devices 102 and 109 are considered to be over-the-wire devices or components and may be nestable within each other, fit over each other or interlock at one or more positions. The devices 102 and 109 may each include a hub 106 (or may share a hub) that may be configured within the devices 102 or 109, applied (connected/coupled) to the devices 102 or 109 or configured to fit within the devices 102 or 109.

The shape sensing system 104 includes one or more optical fibers which may be arranged in a set pattern or patterns. Optical fibers of shape sensing system 104 connect to the workstation 112 through cabling 126. The cabling 126 may include fiber optics, electrical connections, other instrumentation, etc., as needed.

System 104 with fiber optics may be based on fiber optic Bragg grating sensors, Rayleigh scattering, or other types of scattering. Inherent backscatter in conventional optical fiber can be exploited, such as Raleigh, Raman, Brillouin or fluorescence scattering. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in one or more cores running within a single length of multi-core fiber, or in multiple single-core fibers arranged together, the 3D shape and dynamics of the surface of interest can be followed.

A fiber optic Bragg grating (FBG) system may also be employed for system 104. FBG is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

Fresnel reflection at each of the interfaces where the refractive index is changing is measured. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors.

Incorporating one or more cores permits a three dimensional form of such a structure to be precisely determined. From the strain measurement, the curvature of the structure can be inferred at that position. From the multitude of measured positions, the total three-dimensional form is determined. A similar technique can be used for multiple single-core fibers configured in a known structure or geometry.

In one embodiment, workstation 112 is configured to receive feedback from the shape sensing device 104 and record accumulated position data as to where the sensing device 104 has been within a volume 130. The shape sensing information within the space or volume 130 can be displayed on a display device 118. Workstation 112 includes the display 118 for viewing internal images of a subject (patient) or volume 130 and may include shape images 134 as an overlay on medical images 136 such as x-ray images, computed tomography (CT) images, magnetic resonance images (MRI), real-time internal video images or other images as collected by an imaging system 110 in advance or concurrently. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

A registration module 144 is stored in memory 116 and is configured to register a target node(s) 124 in the shape information to the over-the-wire devices 102 and/or 109. The target node(s) 124 may include any identifying features on the device 102 that can be employed as a reference, for example, a hub(s) 106, temperature changing elements, shear wave producing elements, etc. The devices 102 and 109 and the target node(s) 124 are preferably visualized in the image or images 136, either directly or virtually (e.g., represented by a virtual model). In addition, a virtual model 146 of the over-the-wire devices 102 and 109 may be rendered using the target node(s) 124 as a reference to visualize in the over-the-wire devices 102 and 109 in images rendered on the display 118. The registration module 144 can be employed to compute or estimate the geometric relationship (s) between the devices 108, 102 and/or 109.

In one embodiment, the hub 106 or other reference is registered to the target node 124 in the over-the-wire devices 102 and/or 109 by attaching the hub 106 to a proximal portion of the over-the-wire device 102 and/or the device 109 to enable a registration (e.g., longitudinal) between the shape sensed guidewire 108 and the over-the-wire devices 102, 109. To create a meaningful visualization of the over-the-wire devices 102, 109, the over-the-wire devices 102, 109 can be virtually rendered at the locations of the identified device nodes. Nodes 124 can also be considered to be device features of interest to the clinician. Examples may include a device tip, a position of a fenestration, start and end points of a balloon, location of an ultrasound transducer, etc.

In one embodiment, the target node 124 may include a distinct position of one or more of the devices 102, 109. This node 124 may be employed for positioning many devices and may be employed for safety reasons (e.g., making sure that the tip does not protrude too far into certain vessels that the tip of the device remains inside the vessel, etc.).

Mapping the shape sensed data to the locations of the devices can be done in a plurality of ways. For example, a length of one or both devices 102, 109 may be input to an image processing module 148, which renders a position and dimension(s) of the devices using visualization software. This may be provided by scanning a barcode of the devices 102, 109 (the bar code giving the dimensional information directly or providing the device type's data for look up) and looking up its properties in a database, the user entering a value directly or reading values from a device package, measuring by hand, etc. In another embodiment, the devices 102, 109 may be recognized by the image processing module 148 using an x-ray image and automatically looking up the information from a database. In another embodiment, the devices 102, 109 may be placed and attached to the hub 106 (or hubs) in an x-ray field of view (FOV) and have its length/dimension automatically detected from the resulting image.

This can be done by automatically detecting the device tip in the x-ray image or having the user click on the device tip in an image using e.g., a mouse (120). One or more x-ray projections can be employed, and this can work for all devices. In addition, automatic detection may be performed in other ways, e.g., to know the length, just align the guidewire tip with the tip of the device and click a button, or, loop the tip of the device back onto a known feature on the hub (a divot, for example) and click a button.

In accordance with the present principles, hub 106 provides a straightforward attachment onto a wide range of commercial devices. The function of the guidewire 108 is preserved, e.g., for clinical manipulation such as translation and torqueing. The hub 106 provides an integrated solution for the transfer of data (e.g., hub templates for shape deforming hubs, etc.). In one embodiment, the hub 106 may be employed to create shape deformation in the guidewire 108 that can be used for longitudinal registration. The hub 106 preferably can be retrofit or integrated into to any commercial medical device (102, 109) that runs over a guidewire 108 (or other elongated flexible shape sensed device). For example, the devices 102, 109 may include a catheter, sheath, introducer, endograft deployment system, valve deployment system, transseptal needle, etc. These devices have a wide range of sizes, flexibility and profiles.

The present embodiments provide virtual images of multiple non-shape sensed devices 102, 109, which can run over a single shape sensed device 108. This permits any commercial catheter (manual or robotic), deployment system, sheath, or other such device to be navigated using a shape sensed guidewire (108). The present principles can be applied to many applications such as vascular (catheters, sheaths, deployment systems, etc.), endoluminal (endoscopes or bronchoscopes), orthopedic (k-wires & screwdrivers) as well as non-medical applications.

In one embodiment, a search algorithm in the image processing module 148 may be employed that looks at shape sensed data along the shape sensed device (108) and identifies a template from within the shape data. This could be done fully automatically (search algorithm looks along a straight guidewire and finds the most likely hub or other reference candidate); with user input to confirm the automatically detected hub or reference, or to limit the search range to find the hub or reference, or to position the hub or reference in two different locations (to help the algorithm find the thing that changed); with full user input to select the hub or reference from the shape, with x-ray (or other imaging such as optical, ultrasound, MRI, etc.) to image the hub or reference and then detect the path, etc. The full template can be detected, or a pattern-matching algorithm in the image processing module 148 could match the x-ray view of the hub or reference to potential template matches in a database.

A hub template (deformed shape) may take on any usable shape including 2D or 3D profiles. The hub template needs to be distinguishable from other shape sensing data. In accordance with the present principles, the hub 106 can be employed to determine a reference point for locating the other devices 102 and 109 since these devices 102, 109 do not include their own shape sensing capability. The use of an attachable hub is provided to cause the shape deformation of a shape sensed guidewire or tool through the visual shape representation of a device that is not enabled with shape sensing but that is being used with the shape sensed tool. This permits any commercial catheter (manual or robotic), deployment system, sheath, or other such device to be navigated using a shape sensed guidewire (or other tool). This may be applied to a plurality of useful applications, such as, e.g., vascular (catheters, sheaths, deployment systems, etc.), endoluminal (endoscopes), orthopedic (k-wires and screwdrivers) as well as non-medical applications and also applies to both manual and robotic manipulation of such devices.

In other embodiments, reference points are provided by devices other than or in addition to hubs. In one embodiment, one tracking point 124 may be employed along with a geometric relationship between positions on or between the devices 102, 109. The geometric relationship can include a distance between points of interest or tracking positions 124 on the second device 102 and the third device 109. The geometric relationship can be determined in a plurality of ways and can be computed by one or more of the registration module 144, the image processing module 148, and the optical sensing module 122. Some illustrative examples follow for determining the geometric relationship.

Figure 2:
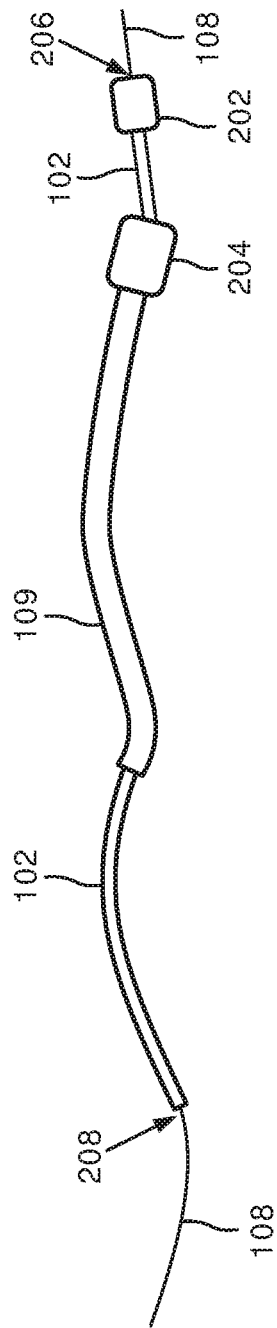
FIG. 2 is a perspective view of a shape sensed device with a plurality of over-the-wire devices in accordance with one embodiment.

Referring to FIG. 2, multiple devices (e.g., device 102 and device 109) run over a single shape-sensed device (device 108) without having to embed shape-sensed fibers into all the devices used in a medical procedure. Deforming the device 108 (e.g., a guidewire) by applying a known curve onto the shape of the guidewire 108 can be employed for locating one or more positions on the guidewire 108 and on one or more other devices 102, 109. It is often difficult to put a known curve into a catheter or sheath because the materials can be stiff and are not easy to deform. Other methods may be needed to determine the location of another device on the guidewire 108 (e.g., device 109).

As previously described, the shape of a non-shape-sensed device 102 can be determined when the non-shape-sensed device 102 runs over a shape-sensed guidewire 108 and locks onto a universal catheter hub 202, e.g., with a Luer lock or other mechanical connection, for example. The shape of the non-shape-sensed device 102 will follow the same shape that is being measured by the shape-sensed device 108. A starting position 206 is where the over-the-wire device 108 locks onto the universal catheter hub 202. An ending position 208 is based on the length of the device which can either be taken as the manufacturer's stated length or from a registration procedure.

Multiple hubs 202, 204 can be connected to multiple over-the-wire devices 102, 109 and still run over the shape sensed device 108. The shape-sensed guidewire 108 and two or more over-the-wire devices 102, 109 that are not shape-sensed, can employ one or more hubs 202 and/or 204.

The types and numbers of devices, hubs and configurations can be employed in any number of combinations. Some illustrative embodiments are described and can be employed. For example, a thermal signature can be employed for gross localization and then a subtle curvature profile can be used for refined localization (in some cases this could even just be a straight section). Additionally, a search range for a second hub (202) can be limited to the range between hub 204 and the entry of the assembly to the body. This makes it significantly easier to locate the tracking feature or node (e.g., temperature, curvature, etc.).

Figure 3:
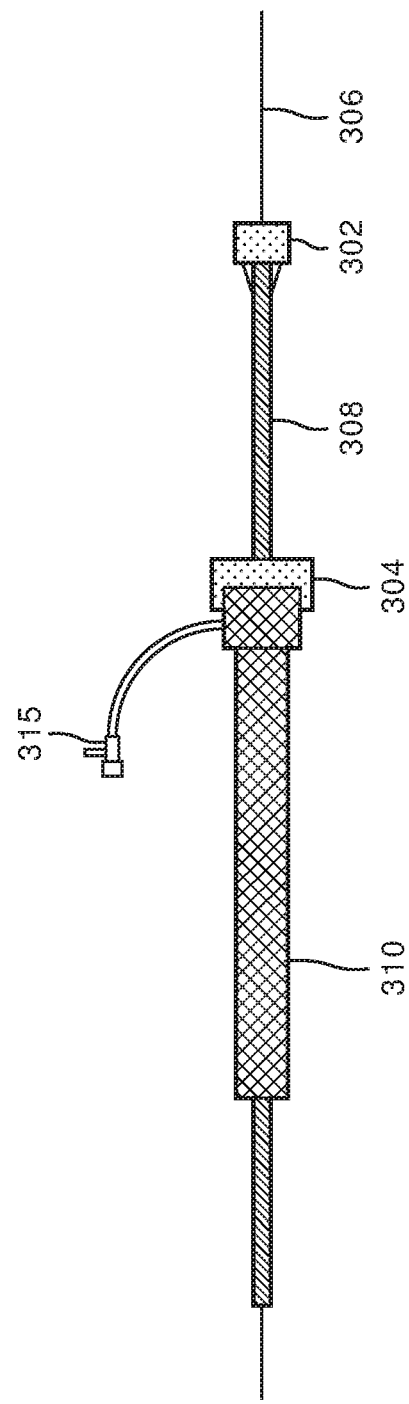
FIG. 3 is a perspective view of a shape sensed device with a plurality of over-the-wire devices including one or more hubs in accordance with one embodiment.

Referring to FIG. 3, in one embodiment, one or more hubs 302, 304 with curvatures in the fiber path can be employed, or a single large hub with two inflection points can be employed. The two hubs 302, 304 illustratively depicted may utilize two universal catheter hubs, one hub 302 running over a device 306 (e.g., a guidewire) and attached to a device 308, the second hub 304 running over device 308 and attached to device 310. These hubs 302, 304 may be static or dynamic hubs to only periodically enable the curvature in device 306. This would reduce the amount of friction felt by the user when moving the devices. The hubs 302, 304 may be configured to operate together so that when one hub is activated, the second hub automatically activates. This could be done mechanically or, more preferably, via electro-mechanical control. Devices 308 and 310 may include additional features 315, such as a siphon tubes, torque arms, locating pins or features, etc.

Figure 4:
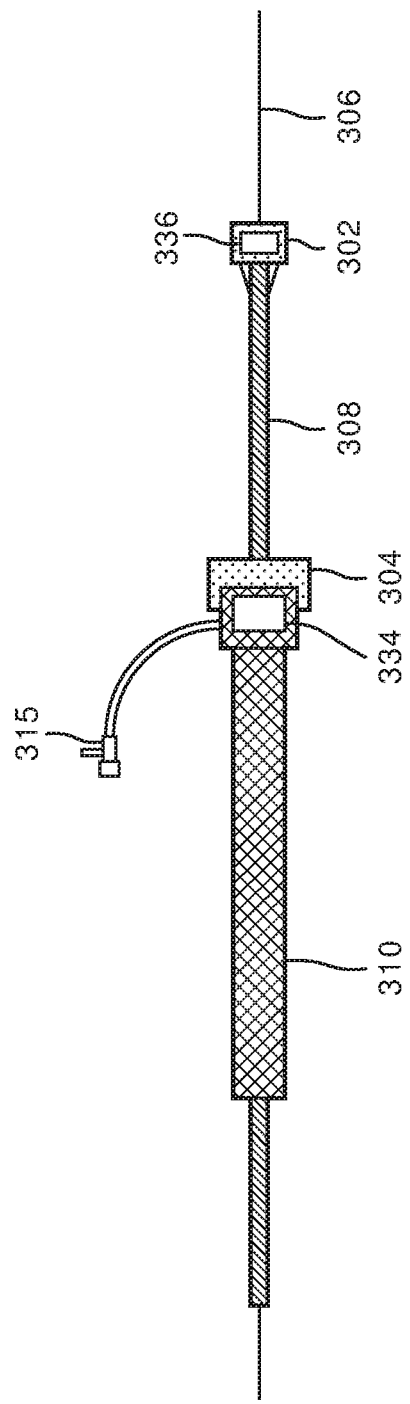
FIG. 4 is a perspective view of a shape sensed device with a plurality of over-the-wire devices having temperature changing elements and/or shear wave producing elements (e.g., piezoelectric elements) in accordance with one embodiment.

Referring to FIG. 4, a change element 334 can be placed on the outside of device 310 at an end portion. The change element 334 can include a temperature change element, or a shear wave change element. The optical fiber embedded in device 306 senses the temperature or shear wave changes at the location where the element 334 is placed. The starting position of device 310 can be identified from this heat or stress field signature. To ensure that the location is properly found and not mistaken for strain or temperature changes due to handling of device 306 (for example, temperature change from the user's fingers) a specific heat pattern or shear wave pattern may be applied. The specific heat pattern may also incorporate cooling elements. A second change element 336 could also be applied to device 308 (in or around hub 302) instead of or in addition to using a universal catheter hub 302 attached to device 308.

In one embodiment, the universal catheter hub 302 is positioned over a device 306 (e.g., a guidewire) and attached to a device 308 (e.g., a catheter) to assist in identifying a relative position of the device 308. The change element 334 is applied to device 310 (e.g., a sheath) to assist in identifying a relative position of the device 310. One disadvantage of using a heating coil lies in its response time. Fast translation of device 310 (and the heating coil) along device 306 may not be captured due to the time needed for the heat to transfer across device 308 and onto the fiber within the device 306.

In one embodiment, the element 334 can be user-enabled. In this way, device 310 needs to only be tracked when the user 'enables' tracking via the element 334. This provides an alternative for devices such as sheaths that are not manipulated as much as catheters and guidewires.

In another embodiment, a piezoelectric element may be employed as element 334 (and/or element 336) and can provide induced shear waves in device 306 when activated. This provides strain due to shear waves and changes the shaped sensing fiber. This can be sensed in shape sensing data. The temperature and shear elements can be employed together or substituted in any combination. The piezoelectric element can also be user-enabled.

Figure 5:
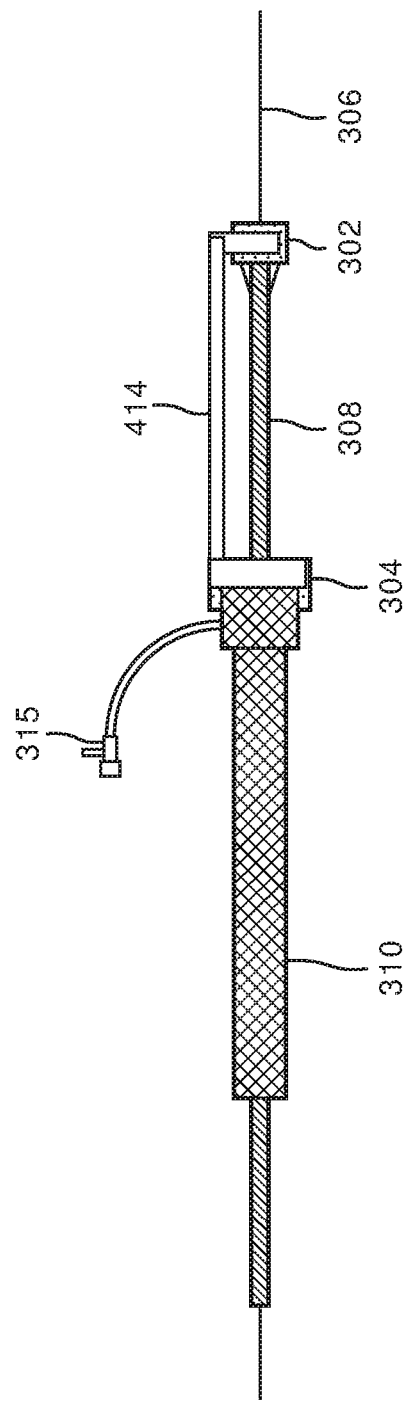
FIG. 5 is a perspective view of a shape sensed device with a plurality of over-the-wire devices having a strain gauge mounted between the over-the-wire devices in accordance with one embodiment.

Referring to FIG. 5, in another embodiment, a universal catheter hub 302 runs over a device 306 (e.g., a guidewire) and attaches to a device 308 (e.g., a catheter). A strain gauge 414 clips onto the universal catheter hub 302 on one end and to a device 310 or hub 304 at the other end of the strain gauge 414. The strain gauge 414 measures the strain electrically to determine a distance between starting positions of device 308 and device 310. The starting position of device 310 for a virtual shape visualization may simply be the starting position of device 308 (obtained from the universal catheter hub 302) plus a distance (e.g., strain gauge length) between device 308 and device 310. An encoded wire spool can be employed instead of the strain gauge 414.

In one embodiment where two hubs are employed, the strain gauge 414 can measure the distance between the two hubs. While the strain gauge 414 is depicted between hubs 302 and 304, the strain gauge can be employed between any of the devices 306, 308, 310 and/or between any device 306, 308, 310 and a hub 302, 304 or combinations of these.

If the shape between the two hubs is not straight then the strain gauge distance will underestimate the actual distance of the beginning of device 310. Shape curvature information obtained from device 306 can be used to correct for this underestimation. One advantage of this embodiment is that it can be simple and low-cost.

Referring to FIG. 6, in another embodiment, a light source 502 is placed on a hub 302. The light source 502 can include a light emitting diode (LED) although any suitable light source may be employed. The light source 502 is attached to or connected with the hub 302 or a Luer lock, etc. of device 308. A reflecting surface 514 is attached to device 310 or hub 304. The reflection of the light of light source 502 from the reflecting surface 514 can be measured by a detector 522 (also attached to the hub 302 or to device 308) and a distance between device 308 and device 310 can be measured or calculated in a similar manner as a laser tape measurement. It should be understood that the reflecting surface and the light source may be placed at different positions and/or on different components (e.g., reversed between hubs 302 and 304, etc.).

Referring to FIG. 7, a universal hub 302 runs over device 306 and is attached to device 308. This universal hub 302 is attached using an encoded slider 604 to device 310 or hub 304. The encoded slider 604 can be implemented as a telescoping device, a linear sliding rail, or other mechanical system that constrains the relative motion between the universal hub 302 and device 310 or hub 304 to an axial translation.

It should be understood that in the embodiments described, many configurations and additional features may be included in addition to or instead of the features depicted. For example, the configuration may include a single hub or multiple hubs. The features may be reversed in direction or orientation. For example, a universal catheter run over a first device and attached to a second device, can be replaced by a second hub attached to a third device and run over the second device (i.e., the configuration can be reversed). The universal catheter hub with a known shape can run over the second device and attach to the third device while the additional hub can be attached to the second device.

Figure 8:
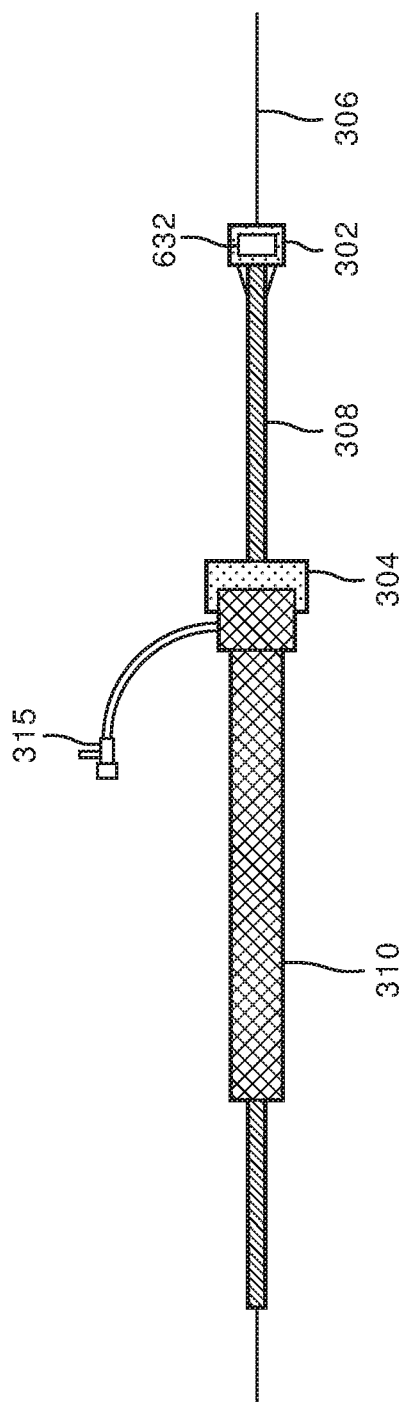
FIG. 8 is a perspective view of a shape sensed device with a plurality of over-the-wire devices having a tracking device on at least one of the over-the-wire devices in accordance with one embodiment.

Referring to FIG. 8, in other embodiments, one or more of the second and third devices 308, 310 may have a start position (i.e., Luer lock or hub 302, 304) tracked using a tracker 632 for tracking technology, e.g., FORS™, optical tracking, electromagnetic (EM) tracking, x-ray opaque materials or any other external tracking method that is registered to the shape sensed device (e.g., guidewire). The tracking technology may be employed to identify one or more tracking nodes on one or more devices. While the tracker 632 is depicted on hub 302, the tracker 632 can alternately be placed on device 306, device 308, hub 304, device 310 or combinations of these.

The hubs as described herein are capable of deforming or otherwise changing a known shape profile of a shape sensing device (e.g., a shape sensed guidewire). The shape sensing may include a FORS™ system that can pass through a lumen of the guidewire or attach outside the guidewire. Although a shape within the hub is described, that shape could alternatively be modified by other methods, e.g., using a heating coil or coils to cause a temperature profile to induce axial strain in the optical shape sensing fiber within the guidewire. The hub may include any combination of path changes (e.g., permanent, heated, reversible) to form a shape profile. The shape profile results in a set hub profile in shape sensed data.

The hubs in accordance with the present principles can operate with a large variety of devices. In addition to catheters, for example, hubs may be employed with endograft deployment devices, etc. Other devices that may be employed with the hubs can include sheaths, introducers, mitral clip delivery systems, mitral valve delivery system, aortic valve delivery systems, therapeutic catheters, balloon catheters, ablation catheters, imaging catheters (intravascular ultrasound (IVUS), optical coherence tomography (OCT), etc.), infusion catheters, endoscopes, needles, etc. While the over-the-wire devices are described as being placed over shape sensed guidewires, the present principles are not limited to a guidewire as the shape sensed device. Instead, any flexible elongated device may be employed and any tool with a shape sensed fiber within it may be employed to infer a shape of another tool.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for shape sensing of multiple over-the-wire devices (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical instrument, comprising:

a first device including a shape-sensed flexible wire that is provided with a fiber optic shape for use in obtaining shape sensing information as a function of a shape of the shape-sense flexible wire along its longitudinal axis;

a second device having a length along its longitudinal axis, wherein the second device is tubular shaped and disposed over the first device for the length of the second device, and wherein a shape of the second device along its longitudinal axis follows the shape of the second device along its longitudinal axis for the length which the second device is disposed over the first device;

a third device having a length along its longitudinal axis, wherein the third device is tubular shaped and disposed over (i) the first device and (ii) a portion of the second device along the length of the third device, wherein a shape of the third device along its longitudinal axis follows the shape of the first device along its longitudinal axis, wherein one of the second device and the third device is registered with respect to the first device at a starting position, and where the second device and third device are registered with respect to each other according to a geometric relationship, wherein positions of the second device and the third device with respect to the first device are determined, via a processor, as a function of (i) the shape sensing information of the first device, (ii) the starting position, and (iii) the geometric relationship; and one of more of (i) one or more temperature changing elements associated with one or more of the second device and the third device to change a temperature at a location where the one or more temperature changing elements is placed and to affect the shape sensing information obtained, via a specific temperature pattern applied to the fiber optic sensor, in response to the temperature change via the one or more temperature changing elements, and (ii) one or more shear wave producing elements associated with one or more of the second device and the third device to generate acoustic shear waves to affect the shape sensing information obtained, via a specific shear wave pattern applied to the fiber optic shape sensor, in response to the acoustic shear waves via the one or more shear wave producing elements, wherein the affected shape sense information is used, via the processor, to locate a position on the first device.

2. The instrument as recited in claim 1, further comprising at least one hub configured to receive the first device, wherein the at least one hub provides a shape profile within the shape sensing information for use, via the processor, to distinguish, within the shape sensing information, a portion of the first device at a position of the at least one hub.

3. The instrument as recited in claim 1, wherein the instrument comprises a temperature changing element associated with one of the second device and the third device, wherein the temperature changing element is configured (i) to change a temperature at a location where the temperature changing element is placed and (ii) to affect the shape sensing information obtained, via a specific temperature pattern applied to the fiber optic shape sensor, in response to the temperature change via the temperature changing element, wherein the affected shape sensing information is used, via the processor, to locate a position on the first device.

4. The instrument as recited in claim 1, wherein the instrument comprises a shear wave producing element, wherein the shear wave producing element includes a piezoelectric element associated with one of the second device and the third device, wherein the piezoelectric element is configured (i) to generate acoustic shear waves at a location where the piezoelectric element is placed and (ii) to affect the shape sensing information obtained, via a specific shear wave pattern applied to the fiber optic shape sensor, in response to the acoustic shear waves via the piezoelectric element, wherein the affected shape sensing information is used, via the processor, to locate a position on the first device.

5. The instrument as recited in claim 1, further comprising a strain gauge secured between two positions on the instrument, wherein a strain measurement of the strain gauge is used, via the processor, to determine a distance between the two positions.

6. The instrument as recited in claim 1, further comprising (i) a light source secured at a first position on the instrument, the first position corresponding to a position of a hub, (ii) a reflector secured at a second position on the instrument, the second position corresponding to a position of a different hub, and (iii) a detector secured at the first position on the instrument, wherein light projected by the light source and reflected from the reflector is measured by the detector to determine, via the processor, a distance between the first and second positions.

7. The instrument as recited in claim 1, further comprising an encoded slider secured between (i) a position on the second device corresponding to a hub, and (ii) a position on the third device, wherein the encoded slider is provided with one of a telescoping device, a linear sliding rail, or other mechanical system, wherein the encoded slider is configured to constrain relative motion between the second device and the third device to an axial translation, and wherein a signal output of the encoded slider is processed, via the processor, to determine a distance measurement between the second device and the third device.

8. The instrument as recited in claim 1, further comprising a tracking device that is provided with one or more tracking nodes, wherein the one or more tracking nodes are (i) coupled to at least one of the first device, the second device and the third device and (ii) registered to the first device, wherein tracking of the one or more tracking nodes, via the tracking device, is used, via the processor, to determine a relative position with the first device.

9. The instrument as recited in claim 1, wherein the first device includes a single guidewire integrated with a shape sensing optical fiber, and wherein the second and third devices include over-the-wire devices.

10. A system with a plurality of over-the-wire devices, comprising:
a medical instrument according to claim 1, including:
a first device including a shape-sensed flexible wire that is provided with a fiber optic shape sensor for use in obtaining shape sensing information as a function of a shape of the shape-sensed flexible wire along its longitudinal axis;
a second device having a length along its longitudinal axis, wherein the second device is tubular shaped and disposed over the first device for the length of the second device, and wherein a shape of the second device along its longitudinal axis follows the shape of the second device along its longitudinal axis for the length which the second device is disposed over the first device;
a third device having a length along its longitudinal axis, wherein the third device is tubular shaped and disposed over (i) the first device and (ii) a portion of the second device along the length of the third device, wherein a shape of the third device along its longitudinal axis follows the shape of the first device along its longitudinal axis, wherein one of the second device and the third device is registered with respect to the first device at a starting position, and wherein the second device and third device are registered with respect to each other according to a geometric relationship, wherein positions of the second device and the third device with respect to the first device are determined, via a processor, as a function of (i) the shape sensing information of the first device, (ii) the starting position, and (iii) the geometric relationship; and
one or more of (i) one or more temperature changing elements associated with one or more of the second device and the third device to change a temperature at a location where the one or more temperature changing elements is placed and to affect the shape sensing information obtained, via a specific temperature pattern applied to the fiber optic sensor, in response to the temperature change via the one or more temperature changing elements, and (ii) one or more shear wave producing elements associated with one or more of the second device and the third device to generate acoustic shear waves to affect the shape sensing information obtained, via a specific shear wave pattern applied to the fiber optic shape sensor, in response to the acoustic shear waves via the one or more shear wave producing elements, wherein the affected shape sensing information is used, via the processor, to locate a position on the first device, and
a shape sensing module coupled to the shape-sensed flexible wire to interpret, via the processor, the shape sensing information to determine positions of the second and third devices relative to the first device.

11. The system as recited in claim 10, further comprising at least one hub associated with one of the second device and the third device and configured to receive the first device, wherein the at least one hub provides a shape profile within the shape sensing information for use, via the processor to distinguish, within the shape sensing information, a portion of the first device at a position of the at least one hub.

12. The system as recited in claim 10, whereing the medical instrument comprises a temperature changing element associated with one of the second device and the third device, wherein the temperature changing element is configured (i) to change a temperature at a location where the temperature changing element is placed and (ii) to affect the shape sensing information obtained, via a specific temperature pattern applied to the fiber optic shape sensor, in response to the temperature change via the temperature changing element, wherein the affected shape sensing information is used, via the processor, to locate a position on the first device.

13. The system as recited in claim 10, wherein the medical instrument comprises a shear wave producing element, wherein the shear wave producing element includes a piezoelectric element associated with one of the second device and the third device, wherein the shear wave producing element is configured (i) to generate acoustic shear waves at a location where the shear wave producing element is placed and (ii) to affect the shape sensing information obtained, via a specific shear wave pattern applied to the fiber optic shape sensor, in response to the acoustic shear waves via the piezoelectric element, wherein the affected shape sensing information is used, via the processor, to locate a position on the first device.

14. The system as recited in claim 10, further comprising a strain gauge secured between two positions on the instrument, wherein a strain measurement of the strain gauge is used, via the processor, to determine a distance between the two positions.

15. The system as recited in claim 10, further comprising (i) a light source secured at a first position on the medical instrument, the first position corresponding to a position of a hub, (ii) a reflector secured at a second position on the medical instrument, the second position corresponding to a position of a different hub, and (iii) a detector secured at the first position on the medical instrument, wherein light projected by the light source and reflected from the reflector is measured by the detector to determine, via the processor, a distance between the first and second positions.

16. The system as recited in claim 10, further comprising an encoded slider secured between (i) a position on the second device corresponding to a hub, and (ii) a position on the third device, wherein the encoded slider is provided with one of a telescoping device, a linear sliding rail, or other mechanical system, wherein the encoded slider is configured to constrain relative motion between the second device and the third device to an axial translation, and wherein a signal output of the encoded slider is processed, via the processor, to determin a distance measurement between the second device and the third device.

17. The system as recited in claim 10, further comprising a tracking device that is provided with one or tracking nodes, wherein the one or more tracking nodes are (i) coupled to at least one of the first device, the second device and the third device and (ii) registered to the first device, wherein tracking of the one or more tracking nodes, via the tracking device, is used, via the processor, to determine a relative position with the first device.

18. The system as recited in claim 10, wherein the first device includes a single guidewire integrated with a shape sensing optical fiber, and wherein the second and third devices include over-the-wire devices.

19. A method for determining positions of over-the-wire devices, comprising:
providing a medical instrument with a first device including a shape-sensed flexible wire that is provided with a fiber optic shape sensor for use in obtaining shape sensing information regarding a shape of the shape-sensed flexible wire along its longitudinal axis; a second device having a length along its longitudinal axis, wherein the second device is tubular shaped and disposed over the first device for the length of the second device, and wherein a shape of the second device along its longitudinal axis follows the shape of the second device along its longitudinal axis for the length which the second device is disposed over the first device; and a third device having a length along its longitudinal axis, wherein the third device is tubular shaped and disposed over (i) the first device and (ii) a portion of the second device along the length of the third device, wherein a shape of the third device along its longitudinal axis follows the shape of the first device along its longitudinal axis;
registering one of the second device and the third device with respect to the first device at a starting position; and
determining a geometric relationship between the second and third devices, wherein a position of the second device and the third device with respect to the first device is determined, via a processor, as a function of (i) the shape sensing information of the first device, (ii) the starting position, and (iii) the geometric relationship,
the method further comprising:
providing the medical instrument with one or more of (i) one or more temperature changing elements associated with one or more of the second device and the third device to change a temperature at a location where the one or more temperature changing elements is placed and to affect the shape sensing information obtained, via a specific temperature pattern applied to the fiber optic sensor, in response to the temperature change via the one or more temperature changing elements, and (ii) one or more shear wave producing elements associated with one or more of the second device and the third device to generate acoustic shear waves to affect the shape sensing information obtained, via a specific shear wave pattern applied to the fiber optic shape sensor, in response to the acoustic shear waves via the one or more shear wave producing elements, wherein the affected shape sensing information is used, via the processor, to locate a position on the first device.

20. The method as recited in claim 19, wherein the geometric relationship is determined by at least one hub configured to receive the first device, wherein the at least one hub provides a shape profile within the shape sensing information for use, via the processor, to distinguish, within the shape sensing information, a portion of the first device at a position of the at least one hub.

21. The method as recited in claim 19, wherein the geometric relationship is determined by a temperature changing element associated with one of the second device and the third device, wherein the temperature changing element is configured (i) to change a temperature at a location where the temperature changing element is placed and (ii) to affect the shape sensing information obtained, via a specific temperature pattern applied to the fiber optic shape sensor, in response to the temperature change via the temperature changing element, wherein the affected shape sensing information is used, via the processor, to locate a position on the first device.

22. The method as recited in claim 19, wherein the geometric relationship is determined by a shear wave producing element, wherein the shear wave producing element includes a piezoelectric element associated with one of the second device and the third device, wherein the piezoelectric element is configured (i) to generate acoustic shear waves at a location where the piezoelectric element is placed and (ii) to affect the shape sensing information obtained, via a specific shear wave pattern applied to the fiber optic shape sensor, in response to the acoustic shear waves via the piezoelectric element, wherein the affected shape sensing information is used, via the processor, to locate a position on the first device.

23. The method as recited in claim 19, wherein the geometric relationship is determined by a strain gauge secured between two positions on the instrument, wherein a strain measurement of the strain gauge is used, via the processor, to determine a distance between the two positions.

24. The method as recited in claim 19, wherein the geometric relationship is determined by a light source secured at a first position on the medical instrument, the first position corresponding to a position of a hub, (ii) a reflector secured at a second position on the medical instrument, the second position corresponding to a position of a different hub, and (iii) a detector secured at the first position on the medical instrument, wherein light projected by the light source and reflected from the reflector is measured by the detector to determine, via the processor, a distance between the first and second positions.

25. The method as recited in claim 19, wherein the geometric relationship is determined by an encoded slider secured between (i) a position on the second device corresponding to a hub, and (ii) a position on the third device, wherein the encoded slider is provided with one of a telescoping device, a linear sliding rail, or other mechanical system, wherein the encoded slider is configured to constrain relative motion between the second device and the third device to an axial translation, and wherein a signal output of the encoded slider is processed, via the processor, to determine a distance measurement between the second device and the third device.

26. The method as recited in claim 19, wherein the geometric relationship is determined by a tracking device that is provided with one or more tracking nodes, wherein the one or more tracking nodes are (i) coupled to at least one of the first device, the second device and the third device and (ii) registered to the first device, wherein tracking of the one or more tracking nodes, via the tracking device, is used, via the processor, to determine a relative position with the first device.

\* \* \* \* \*